US008340250B2

(12) United States Patent
Lemaitre et al.

(10) Patent No.: US 8,340,250 B2
(45) Date of Patent: Dec. 25, 2012

(54) SYSTEM AND METHOD FOR GENERATING X-RAYS

(75) Inventors: Sergio Lemaitre, Whitefish Bay, WI (US); Carey Rogers, Brookfield, WI (US); Yun Zou, Clifton Park, NY (US); Jizhong Chen, Columbia, MD (US)

(73) Assignee: General Electric Company, Schenectady, NY (US)

( * ) Notice: Subject to any disclaimer, the term of this patent is extended or adjusted under 35 U.S.C. 154(b) by 215 days.

(21) Appl. No.: 12/554,164

(22) Filed: Sep. 4, 2009

(65) Prior Publication Data
US 2011/0058643 A1    Mar. 10, 2011

(51) Int. Cl.
*H01J 35/00* (2006.01)
(52) U.S. Cl. ........................................ 378/122; 378/138
(58) Field of Classification Search .................. 378/119, 378/122, 136, 138
See application file for complete search history.

(56) References Cited

U.S. PATENT DOCUMENTS

| 4,104,526 | A | 8/1978 | Albert |
| 5,153,900 | A | 10/1992 | Nomikos et al. |
| 5,617,464 | A | 4/1997 | Mika et al. |
| 6,385,280 | B1 * | 5/2002 | Bittl et al. ........................ 378/16 |
| 6,778,633 | B1 * | 8/2004 | Loxley et al. .................. 378/113 |
| 7,203,269 | B2 * | 4/2007 | Huber et al. .................... 378/10 |
| 7,326,328 | B2 | 2/2008 | Hudspeth et al. |
| 7,388,944 | B2 | 6/2008 | Hempel et al. |
| 2001/0022347 | A1 * | 9/2001 | Katsap et al. .............. 250/492.1 |
| 2006/0115050 | A1 | 6/2006 | Resnick |
| 2007/0053495 | A1 * | 3/2007 | Morton et al. ................ 378/136 |
| 2009/0003529 | A1 | 1/2009 | Zou et al. |

* cited by examiner

*Primary Examiner* — Hoon Song
*Assistant Examiner* — Mona M Sanei
(74) *Attorney, Agent, or Firm* — Ziolkowski Patent Solutions Group, SC (57) ABSTRACT

In one embodiment, an X-ray tube is provided. The X-ray tube comprises at least one thermionic cathode configured to generate an electron beam, a target assembly configured to generate X-rays when impinged with the electron beam emitted from the thermionic cathode, a high voltage supply unit for establishing an output voltage across the thermionic cathode and the target assembly for establishing an accelerating electric field between the thermionic cathode and the target assembly and a mesh grid disposed between the thermionic cathode and the target assembly, the mesh grid configured to operate at a voltage so as to lower the electric field applied at the surface of the thermionic cathode. Further, the voltage at the mesh grid is negatively biased with respect to the voltage at the thermionic cathode.

28 Claims, 7 Drawing Sheets

SYSTEM AND METHOD FOR GENERATING X-RAYS

FIELD OF INVENTION

The invention generally relates to diagnostic imaging systems and more particularly to X-ray tube used in imaging systems.

BACKGROUND OF THE INVENTION

X-ray generating systems typically include an electron generating cathode and an anode assembly in a sealed housing. The cathode provides an electron stream or current that is directed towards the anode assembly. This focused electron beam is accelerated across the anode-to-cathode vacuum gap and produces X-rays upon impact with the anode. Because of the high power density generated at the location where the electron beam strikes the anode, it is desirable to rotate the anode assembly. Many X-ray tubes therefore include a rotating anode structure for distributing the heat generated at a focal spot.

The requirements for X-ray tubes used in computed tomography have steadily grown with the manifold possibilities of computed tomography. Modern computed tomography systems require X-ray tubes that allow the X-ray current thereof to be modulated with high speed, for example, to be able to achieve an optimized dose modulation or operation at two different energies with an equilibrium photon flow (flux).

One of the limitations associated with the high power imaging X-ray tubes described in the prior art is unavailability of fast gridding or current modulation. In order to change the electron beam current, the method suggested in the prior art is to adjust the temperature of a filament in the cathode. However, this is a slow process and the time scale of changing the temperature is in millisecond range. This fails to keep pace with view-to-view frame change, where the requirement for current modulation is in a span of microseconds.

Another method described in the prior art involves placing an aperture plate opposite to cathode in order to change the emission. The voltage changes on the aperture plate influences the emission from the cathode. However, one issue related to this method is the focal spot change when the emission current is modulated. By using a mesh grid, the focal spot size change can be reduced. Meshes to grid electron emission are e.g. used in microwave amplifiers. The mesh grid controls the path of the electron beam and focuses the beam. The time response is greatly improved by the addition of the mesh grid to control the emitted electrons from the cathode by means of varying the potential applied at the mesh grid.

The mesh grid typically comprises a two-dimensional high transparency grid with uniform mesh spacing in both dimensions. Providing such mesh grid minimizes the interception of beam electrons by increasing the mesh transparency. However, beam electrons may interact with the mesh grid, across the total beam cross section. This has the undesirable effect of beam loss, beam degradation and mesh degradation.

Moreover, the mesh grids employed are typically positively biased with respect to the cathode. Consequently, electrons emitted from the cathode may reach the mesh grid and degrade the mesh grid by overheating due to electron bombardment.

Therefore, it would be desirable to have an apparatus and method for minimizing the voltage necessary for extraction of the electron beam from the cathode, while still allowing fast modulation of the beam current for sufficient focusing of the electron beam so as to form a usable focal spot on a target. In particular, it would be desirable to have a mesh grid that allows for efficient low voltage extraction and beam focusing.

BRIEF DESCRIPTION OF THE INVENTION

The above-mentioned shortcomings, disadvantages and problems are addressed herein which will be understood by reading and understanding the following specification.

In one embodiment, an X-ray tube for an imaging system is provided. The X-ray tube comprises at least one thermionic cathode configured to generate an electron beam, a target assembly configured to generate X-rays when impinged with the electron beam emitted from the thermionic cathode, a high voltage supply unit for establishing an output voltage across the thermionic cathode and the target assembly for establishing an accelerating electric field between the thermionic cathode and the target assembly and a mesh grid disposed between the thermionic cathode and the target assembly, the mesh grid configured to operate at a voltage so as to decrease the electric field at the surface of the thermionic cathode. Further, the voltage at the mesh grid is essentially negatively biased with respect to the voltage at the thermionic cathode.

In another embodiment a CT system is provided. The CT system comprises a rotatable gantry having an opening for receiving an object to be scanned, an X-ray tube coupled to the gantry and configured to project X-rays through the opening and a detector assembly coupled to the gantry and positioned to receive X-rays that pass through the object to be scanned. The X-ray tube comprises at least one thermionic cathode configured to generate an electron beam, a target assembly configured to generate X-rays when impinged with the electron beam emitted from the thermionic cathode, a high voltage supply unit for establishing an output voltage across the thermionic cathode and the target assembly for establishing an accelerating electric field between the thermionic cathode and the target assembly and a mesh grid disposed between the thermionic cathode and the target assembly, the mesh grid configured to operate at a voltage so as to enhance the electric field at the surface of the thermionic cathode. Further, the voltage at the mesh grid is essentially negative biased with respect to the voltage at the thermionic cathode.

In yet another embodiment, a method of X-ray imaging is provided. The method comprises arranging a thermionic cathode and a mesh grid to support a grid-cathode voltage therebetween to extract a plurality of electrons from the thermionic cathode to form an electron beam, modulating the grid-cathode voltage so as to control an amperage of the electron beam, establishing an output voltage across the thermionic cathode and a target assembly to accelerate the electron beam toward the target assembly to generate X-rays therefrom, the target assembly positioned such that the X-rays emit toward an object, receiving a set of imaging data indicative of an amount of attenuation of the X-rays after having passed through the object and reconstructing an image of the object based on the imaging data received. Further the voltage at the mesh grid is essentially negatively biased with respect to voltage at the thermionic cathode.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Devices for generation of X-ray radiation are used, for example, in medical diagnostics in order to acquire radiographic images or, in case of computed tomography (CT), internal images of the body.

The operating environment for the invention is described with respect to a sixty-four-slice computed tomography (CT) system. While described with respect to a "third generation" CT scanner, the invention is equally applicable with other CT systems. Additionally, it will be appreciated by those skilled in the art that the invention is equally applicable for use with other applications in which an electron gun is implemented.

Figure 1:
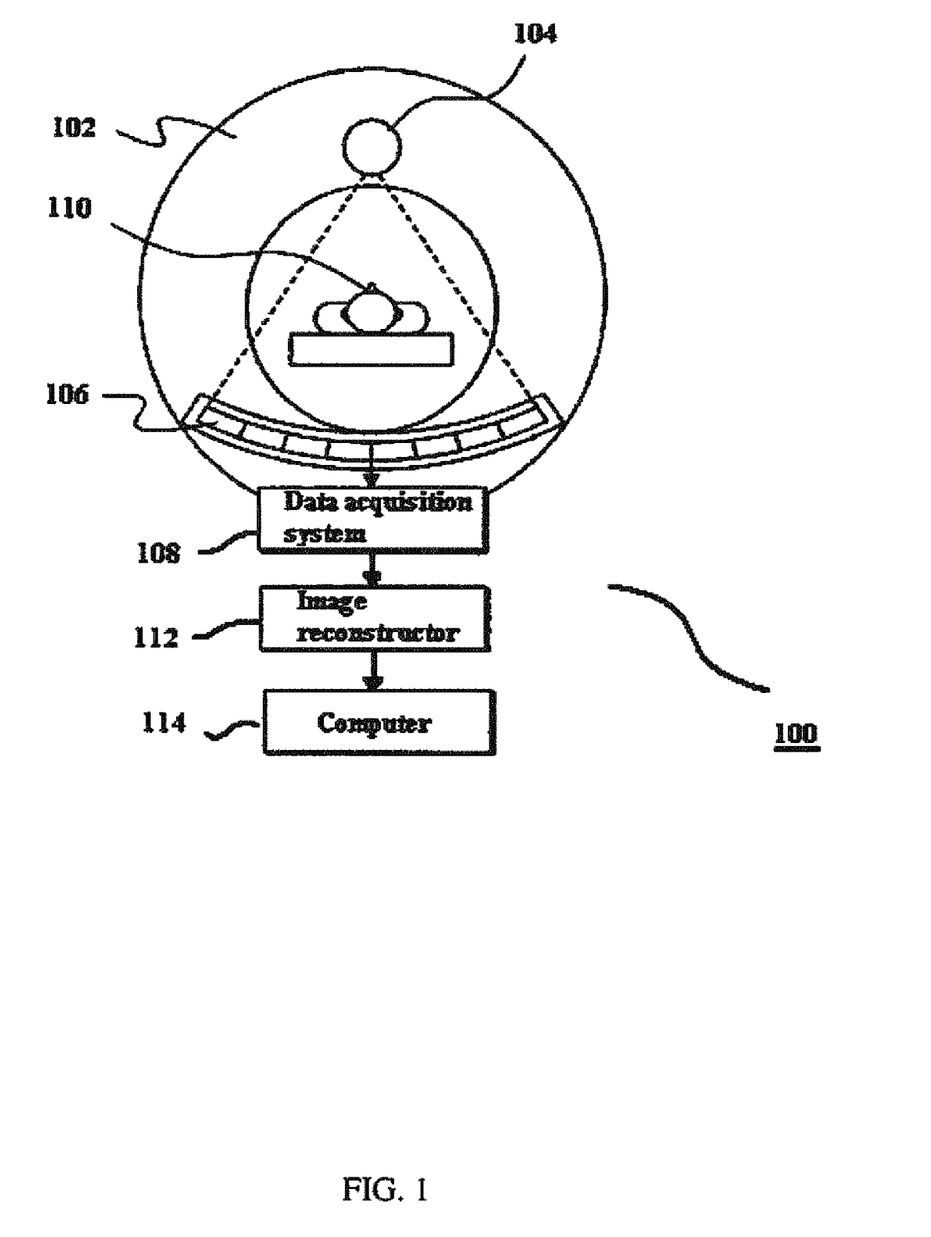
FIG. 1 shows a schematic diagram of a CT system as described in an embodiment.

Referring to FIG. 1, a computed tomography (CT) imaging system 100 is shown as including a gantry 102 representative of a "third generation" CT scanner. The gantry 102 is coupled with an X-ray tube 104 that projects a beam of X-rays towards a detector assembly on the opposite side of the gantry 102. The detector assembly is formed by a plurality of detectors 106 and a data acquisition system 108 (DAS). The plurality of detectors 106 sense the projected X-rays that pass through a patient 110, and the DAS 108 converts the data to digital signals for subsequent processing. Each detector 106 produces an analog electrical signal that represents the intensity of an impinging X-ray beam and hence the attenuated beam as it passes through the patient 110. During a scan to acquire X-ray projection data, gantry 102 and the components mounted thereon rotate about a center of rotation.

An image reconstructor 112 receives sampled and digitized X-ray data from DAS 108 and performs high-speed reconstruction. The reconstructed image is applied as an input to a computer 114, which stores the image in a mass storage device.

Figure 2:
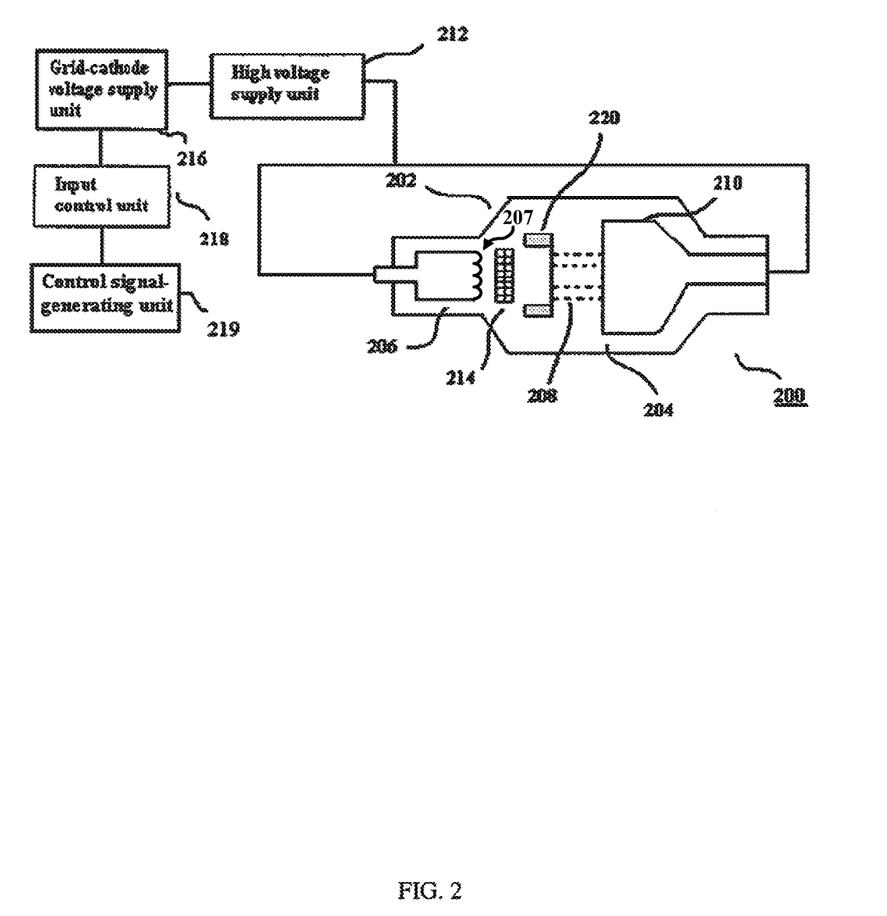
FIG. 2 shows a schematic diagram of an X-ray tube as described in one embodiment.

With continuing reference to FIG. 1 and with further reference to FIG. 2, which schematically shows components of the X-ray tube 200 (same as 104 in FIG. 1) in cross-section, the X-ray tube 200 comprises a housing 202 having a vacuum gap 204 that encloses at least one thermionic cathode 206 configured to generate an electron beam 208 and a target assembly 210 configured to generate X-rays when impinged with the electron beam 208 emitted from the thermionic cathode 206. The X-ray tube 200 further comprises a high voltage supply unit 212 for establishing an output voltage across the thermionic cathode 206 and the target assembly 210 for establishing an accelerating electric field between the thermionic cathode 206 and the target assembly 210.

The thermionic cathode 206 (also referred to herein as cathode) comprises an Elongated wire filament having a plurality of coil windings 207 with a wire diameter of 8-10 mil, arranged in a cathode cup of the thermionic cathode 206. The thermionic cathode 206 generates electrons by thermionic emission, in response to an input current delivered by the high voltage supply unit 212. An isolation transformer and insulating standoffs (not shown) may electrically isolate the thermionic cathode 206 from other elements of the X-ray tube 200. The electron beams 208 generated by the thermionic cathode 206 collectively produce electron beam current (also referred to herein as cathode current, emission current, electron current etc.).

In order to generate an X-ray beam of sufficient strength for CT and other X-ray based diagnostic imaging modalities, cathode assemblies of X-ray tube 200 typically provide approximately 1 ampere of electron current. The electrons emitted from the cathode 206 are accelerated across the vacuum gap 204 of the X-ray tube 200 to the target assembly 210 by voltages in the order of 20 to 150 kVp. To achieve high temperatures needed for electron emission from the thermionic emitter, for example, a heater voltage of about 10 V is applied across the thermionic emitter, producing a heater current of about 7 amps in the thermionic cathode 206. Therefore, adjustments to the heater voltage and/or heater current applied at the cathode 206 regulate the electron beam current emitted from the thermionic emitter.

The time response of electron beam current due to changing heater current is in the order of milliseconds. To improve the time response by a factor of about 1000 a wired mesh 214 is disposed between the target assembly 210 and the thermionic cathode 206. The mesh grid 214 extends across an opening at a desired distance from the thermionic cathode 206. A relatively small negative voltage applied to the mesh grid 214 with respect to the thermionic cathode 206 is used to suppress the electron beam current emitted from the thermionic emitter. The suppression voltage can be adjusted within microseconds.

Figure 3:
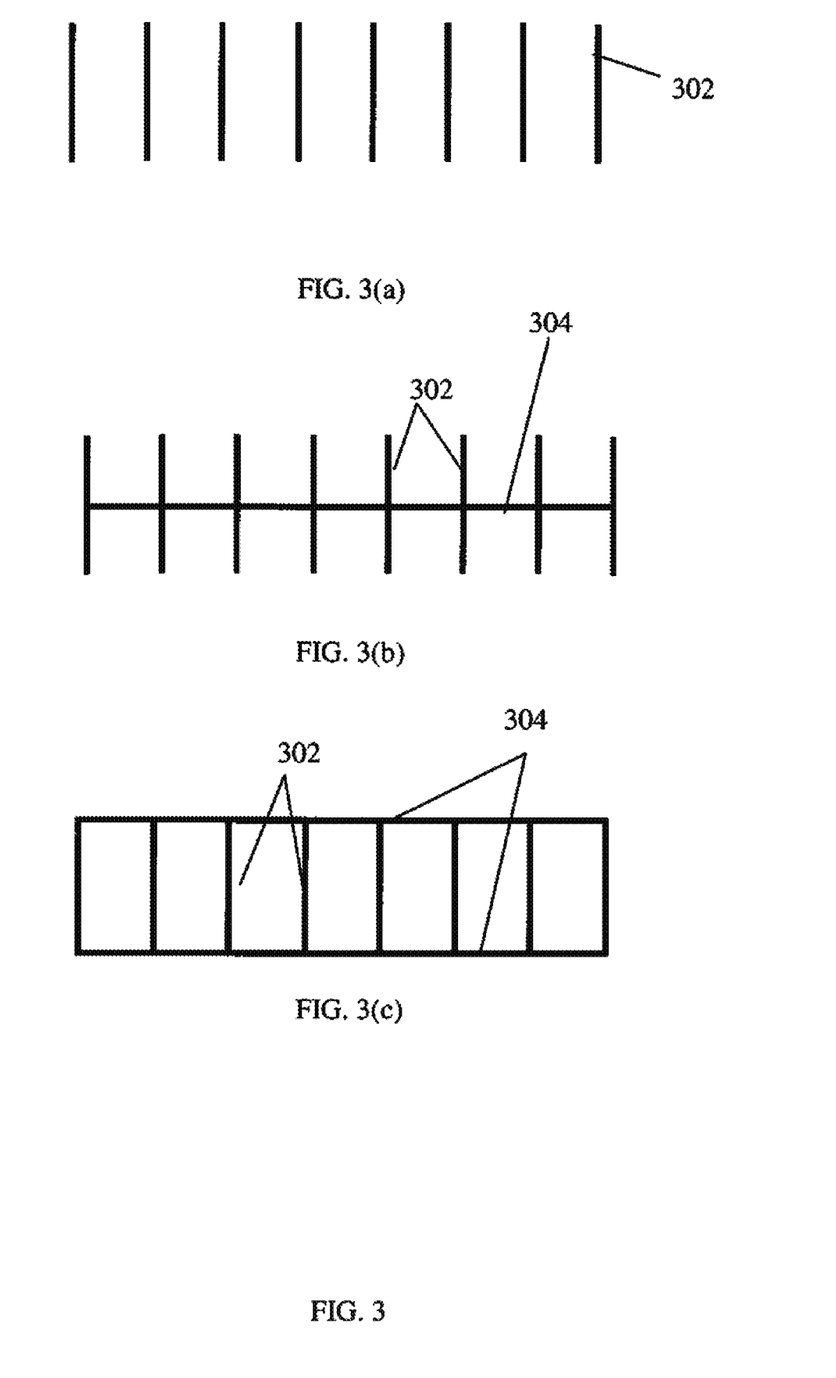
FIG. 3 shows front view and top view schematic diagrams of an arrangement of thermionic cathode and mesh grid as described in one embodiment.

The mesh grid 214 can be of different shape and configuration, as can be seen from various examples of the mesh grid 214 shown in FIG. 3. The mesh grid 214 comprises a plurality of grid members 302 positioned within a support structure (not shown). The grid members 302 can be metallic wires. The wires 302 employed in the mesh grid 214 can be of substantial ruggedness. For example for typical thermionic cathode 206, the diameter of the coil windings is in the range of about 0.25 mm and the diameter of the wire of the mesh grid 214 can be in the range of about 0.1 mm. The mesh grid 214 can be placed at a macroscopic distance in the range of about 0.1 mm-1 mm from the thermionic cathode 206 allowing for good manufacturability. More particularly, the mesh grid 214 is placed at a distance in the range of about 0.25 mm to 0.5 mm from the thermionic cathode 206.

The plurality of wires 302 are spaced apart at a desired distance from one another to form a plurality of openings in the mesh grid 214 through which electrons in the electron beam 208 are transmitted. The plurality of wires 302 that form the mesh grid 214, however, also intercept beam current from the electron beam 208, which causes degradation in the beam quality and negatively impacts formation of a usable focal spot on the target assembly 210. That is, the increased beam emittance of the electron beam 208 subsequent to the electron beam 208 hitting the mesh grid 214 prevents the electron beam 208 from being focused to a small spot on the target assembly 210.

To further reduce the amount of beam current intercepted by the mesh grid 214, the mesh grid 214 is constructed as a one-dimensional grid. That is, wires 302 used to form mesh grid 214 are aligned directionally parallel in a single direction. The grid members 302, in one-dimensional mesh grid 214, are machined to a predetermined shape so as to control the electron beam characteristics. This enables the one-dimensional mesh grid 214 to focus the electron beam 208 received from the thermionic cathode 206 into a desired spot size. The width of each of the plurality of wires 302 and the spacing between the wires 302 can vary, but in one embodiment, the wire width is 0.05 mm and the spacing between each of the wires 302 is 0.38 mm.

As shown in FIG. 3, the mesh grid 214 is formed as a non-circular, essentially rectangular grid having a high aspect ratio of length to width. For example, the mesh grid 214 may have an aspect ratio of 2×8 mm, such that the width is 2 mm and the length is 8 mm. The parallel-aligned wires 302 are positioned such that they run across the width of the high aspect ratio mesh grid 214. The one-dimensional arrangement of the wires 302 allows for a greater percentage of beam electrons to pass through the mesh grid 214 without being intercepted and provides for minimum degradation of the electron beam 208 in a direction parallel to the plurality of wires 302. That is, the one-dimensional grid allows for high compression of the electron beam 208 in the direction parallel to the plurality of wires 302 and focusing of the electron beam 208 into a desired spot size.

In another embodiment, as shown in FIG. 3, the mesh grid 214 can include one or more cross-wires 304 (i.e., support wires) that are oriented perpendicularly to the plurality of parallely positioned wires 302. The one or more cross-wires 304 run across the length of the high aspect ratio mesh grid 214 and function to provide and improve the mechanical strength and thermal stability of the mesh grid 214. While the number of cross-wires 304 can vary, the greater the number of cross-wires 304, the more the beam quality will be compromised. A trade-off between mechanical strength and beam quality can be examined when selecting the number of cross-wires 304 to implement into the one-dimensional mesh grid 214. However, it is to be noted that, in terms of beam quality, the one-dimensional mesh shown in FIG. 3(a) has less affect on the beam focal spot size change.

Figure 4A:
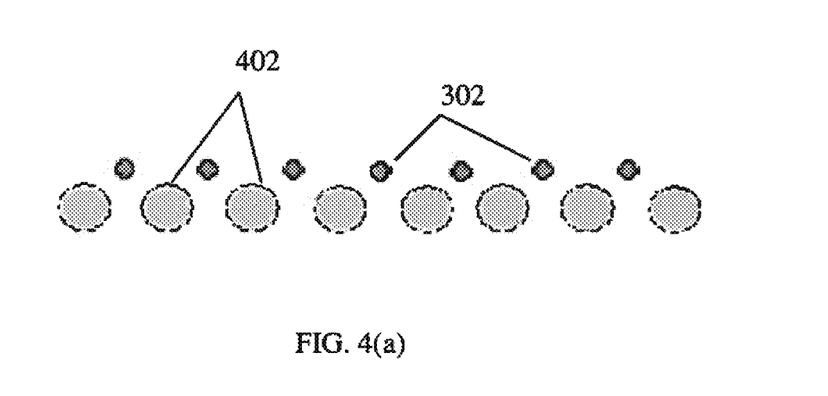
FIG. 4 shows schematic diagrams of the mesh grid as described in three different embodiments.
Figure 4B:
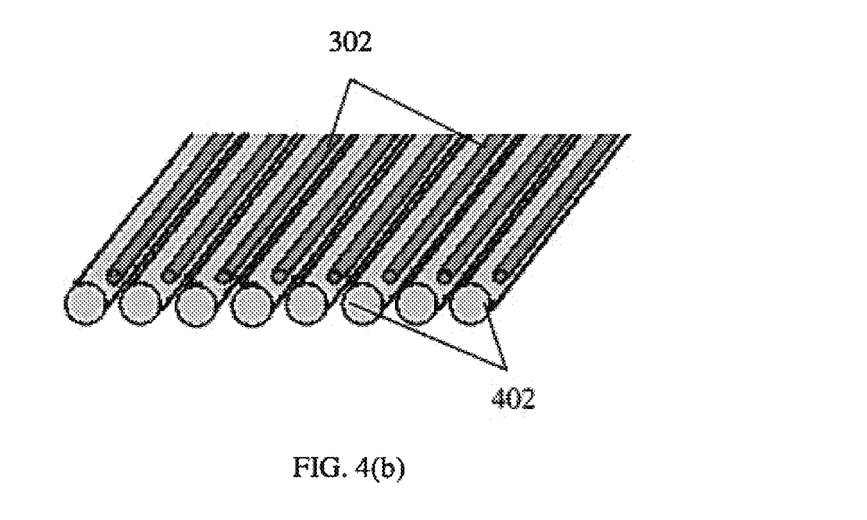

In one embodiment, the invention provides a grid geometry that conforms with the geometry of the thermionic cathode 206, the grid geometry being the geometry of the mesh grid 214. As shown in FIG. 4, the thermionic cathode 206 comprises a plurality of macro-emitters 402. In one embodiment, the amount of beam current intercepted by the mesh grid 214 can be reduced, and degradation in the beam quality minimized, by aligning the multiple macro-emitters 402 with openings in the mesh grid 214. In other words, the mesh grid 214 comprises wires 302 that are aligned with the gaps between successive coil windings of the thermionic cathode 206. The space between two successive coil windings is expected to record relatively less emission of the electron beam 208 when compared to the emission of the electron beam 208 right across the coil windings. Such an alignment facilitates passage of a substantially higher percentage of electrons through the mesh grid 214.

Further, it is possible to increase the diameter of the wires 302 and 304 employed in the mesh grid 214 without significant increase in electron bombardment. Thus the mesh grid 214 can be more robust. Thus, due to minimal interaction with the electron beam 208, the conformal mesh design allows better electron beam quality. Further, the large diameter of the wires 302 and 304 employed in the mesh grid 214 ensures good robustness.

In another embodiment, another technique is described to reduce the beam degradation occurring as a result of interception of the electron beam current by the mesh grid 214. The technique describes designing beam optics so as to operate the mesh grid 214 at an approximate zero or negative voltage relative to the thermionic cathode 206. In such a scenario, the electron beam energy that is deposited on the mesh grid 214 is substantially low.

Accordingly, with continuing reference to FIG. 1 and FIG. 2, the X-ray tube 200 further comprises a grid-cathode voltage supply unit 216 coupled between the mesh grid 214 and the thermionic cathode 206 to establish a voltage difference there between. The amplitude of the voltage at the mesh grid 214 is a predetermined function of time and is maintained in the range of about +100V to −5000V relative to the voltage at the thermionic cathode 206. Further, the grid-cathode voltage supply unit 216 is configured to control time variation in the amplitude of the voltage applied at the mesh grid 214.

In one embodiment, the grid-cathode voltage supply unit 216 is configured to maintain the voltage at the mesh grid 214 at a high negative potential and to maintain the voltage at the thermionic cathode 206 substantially at an electrical ground potential.

In one embodiment, the voltage at the mesh grid 214 can be a train of pulses. Accordingly, the electron beam current emitted from the cathode 206 can as well be a train of pulses. The amplitude of the voltage at the mesh grid 214 being a predetermined function of the time; any variation in the time or duty cycle of the voltage can result in modulation of the electron beam current emitted from the thermionic cathode 206. The average current is the peak current multiplied by the duty cycle. Therefore, a change in the duty cycle results in proportional variation of the average current. Thus, the duty cycle of the train of pulses representing the voltage at the mesh grid 214 can be varied to modulate the average electron beam current.

In order to control time variation of the voltage at the mesh grid 214, the X-ray tube 200 further comprises an input control unit 218 coupled to the grid-cathode voltage supply unit 216. The input control unit 218 is configured to vary selectively the magnitude of the voltage difference between the thermionic cathode 206 and the mesh grid 214 to maintain the electron current flow from the thermionic cathode 206 to the target assembly 210 at a predetermined value. To measure and obtain feedback about the electron beam current, the X-ray tube 200 further comprises a control signal-generating unit 219 coupled to the input control unit 218. The control signal-generating unit 219 is configured to generate control signals representative of the magnitude of the electron current flow from the thermionic cathode 206 to the target assembly 210. Inside the control-signal generating unit 219, the electron beam current emitted by the thermionic cathode 206 may be sensed by a sensing resistor (not shown) positioned in series with the thermionic cathode 206 thereby giving rise to a control signal which may be measured or fed back to the input control unit 218 so as to regulate the voltage applied at the mesh grid 214.

Figure 5:
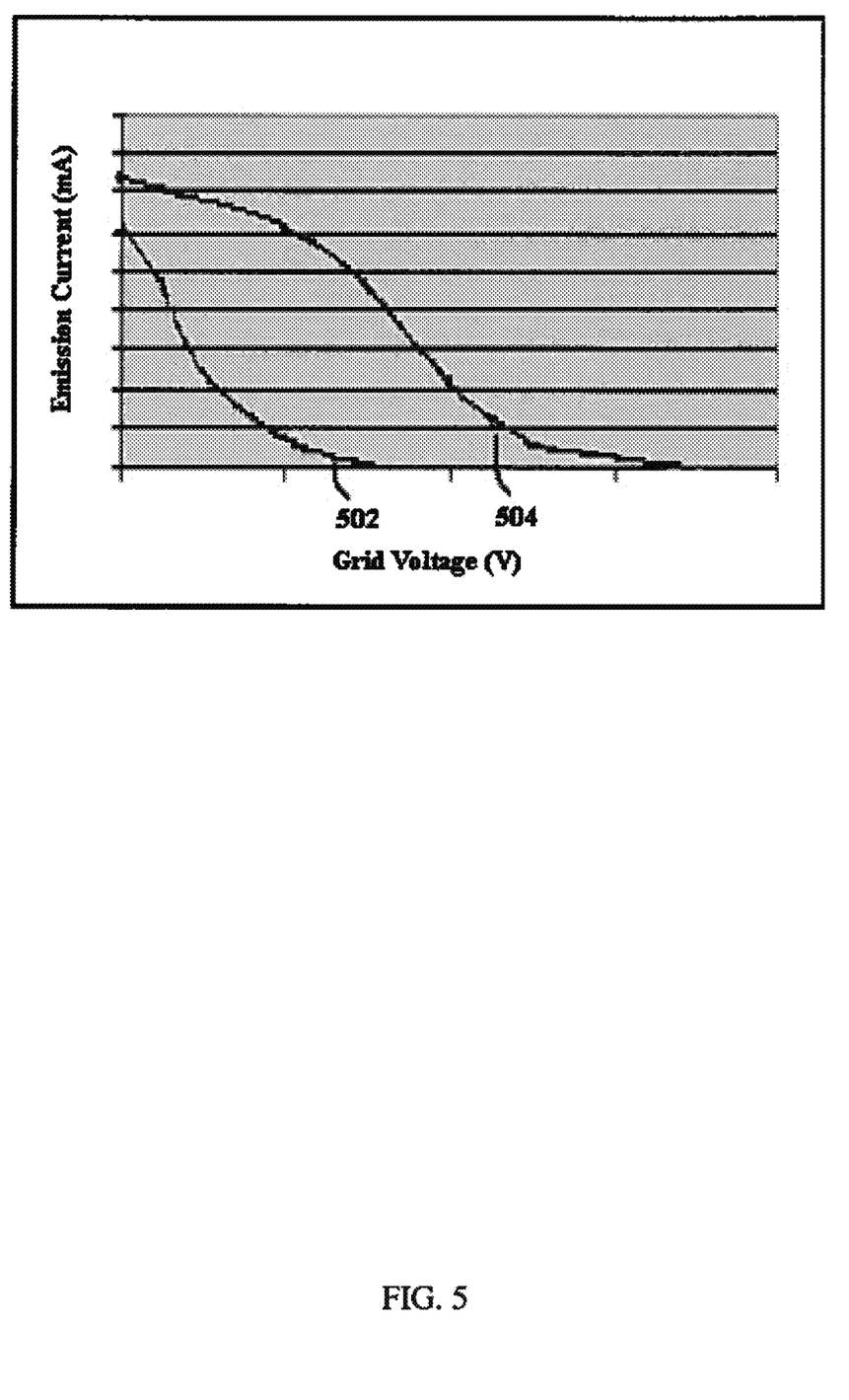
FIG. 5 shows a graphical representation of the cathode current emission for different beam energies.

FIG. 5 shows a simulated cathode current change corresponding to a change in the voltage at the mesh grid 214 for two different beam energies. The curve 502 represents the cathode current emission corresponding to a beam energy equivalent to 80 kV and the curve 504 represents the cathode current emission corresponding to a beam energy equivalent to 140 kV. The simulation shows that the emission current can be effectively modulated by controlling the voltage at the mesh grid 214. The cathode current emission is largest when the voltage at the mesh grid 214 is approximately equal to the voltage at the thermionic cathode 206. However, as the voltage at the mesh grid 214 moves towards negative with respect to the voltage at the thermionic cathode 206, the cathode current emitted from the cathode 206 reduces.

Due to close proximity of the mesh grid 214 to the thermionic cathode 206, the electron beam current can be efficiently controlled by applying relatively small negative bias voltages (range of hundreds of volts) thereby yielding very rapid changes (range of micro seconds) in the electron beam current.

Referring to the technique described above, modulation of the duty cycle or time variation of the voltage applied at the mesh grid 214 causes modulation of the electron beam current generated at the thermionic cathode 206. A pulsed electron beam emission with a variable pulse width therefore can be achieved by suitable control of the voltage applied at the mesh grid 214. The modulation in the intensity of the electron beam current emitted by the thermionic cathode 206 causes dose modulation in the X-ray dose delivered to the patient 110.

The technique of dose modulation in the X-ray delivered to the patient 110, as described herein, mitigates a concern in computed tomography imaging associated with limiting X-ray exposure of the patient 110. In medical imaging applications, the X-ray dosage delivered to the patient 110 is a regulated safety parameter. The intensity of the X-ray beam is adjusted to maintain a constant radiation dose for each axial slice or each helical rotation as an imaging scan passes through regions of the body having differing X-ray absorption densities. In airport security scanning, the X-ray intensity is advantageously adjusted to account for differing X-ray absorption characteristics of different types of luggage. Thus, the technique of dose modulation described herein enables adjustment in the X-ray intensity based on the type of application of the generated X-rays.

Further, advantageously, changing the thermionic cathode current does not significantly alter the focus of the electron beam 208 or change the size of the focal spot. The proximity of the mesh grid 214 to the cathode 206 and the geometry of the mesh grid 214 facilitate efficient modulation of the electrical field at the cathode 206 without focal spot degradation. Thus, the technique described herein can modulate the electron beam current from full emission down to complete cut off while maintaining focal spot characteristics constant for all intermediate cathode current levels.

Still referring to FIG. 2, to effect beam wobble, the X-ray tube 200 includes one or more focus electrodes 220 arranged on opposite sides of the thermionic cathode 206. The focus electrodes 220 are biased with an alternating polarity to generate a switched electrostatic force orthogonal to the electron beam 208 that shifts the electron beam 208 between two paths corresponding to the two focal spots of the wobble. Alternatively, an orthogonal electromagnetic force can be used to switchingly steer the beam. The focus electrodes 220 along with the mesh grid 214 enable simultaneous gridding and focusing of the electron beams 208 as the electron beams 208 progress toward the target assembly 210.

In one embodiment, a first pair of focus electrodes 220 control length of the focal spot and a second pair of focus electrodes 220 control width of the focal spot. During the modulation of the electron beam current, the voltage applied at the focus electrodes 220, to control width and length of the focal spot, is also changed to compensate for the focal spot size change.

Figure 6:
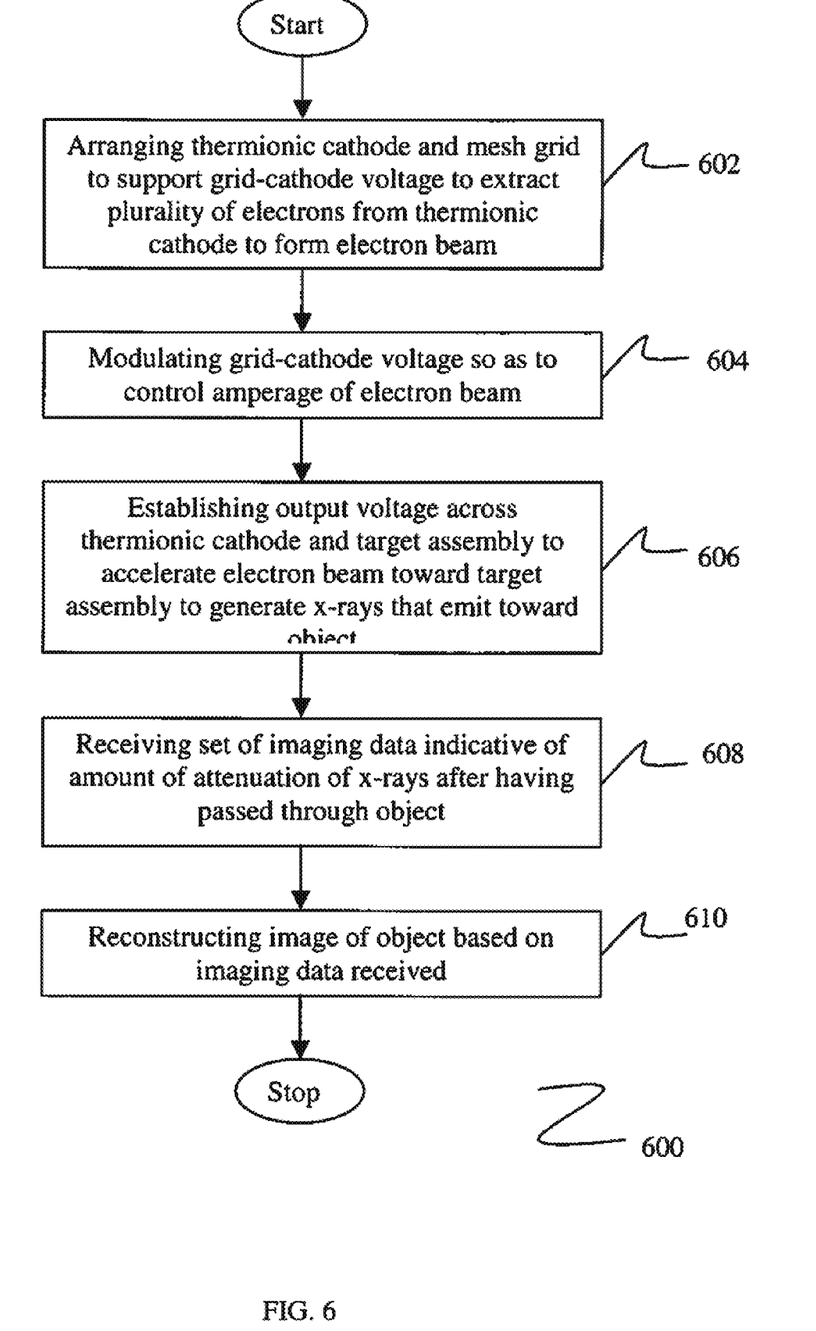
FIG. 6 shows a flow chart representing method of X-ray imaging as described in one embodiment.

In another embodiment, as shown in FIG. 6, a method 600 of X-ray imaging is provided. The method 600 comprises steps of arranging the thermionic cathode 206 and the mesh grid 214 to support a grid-cathode voltage therebetween to extract a plurality of electrons from the thermionic cathode 206 to form an electron beam 208 at step 602. The grid-cathode voltage is the voltage difference applied between the mesh grid 214 and the thermionic cathode 206 by the grid-cathode voltage supply unit 216.

The method 600 further comprises modulating the grid-cathode voltage so as to control an amperage of the electron beam 208 at step 604, establishing an output voltage across the thermionic cathode 206 and the target assembly 210 to accelerate the electron beam 208 toward the target assembly 210 to generate X-rays at step 606, the target assembly 210 being positioned such that the X-rays emit toward the patient 110, receiving a set of imaging data indicative of an amount of attenuation of the X-rays after having passed through the patient 110 at step 608 and reconstructing an image of the patient 110 based on the imaging data received, at step 610. Further, the voltage at the mesh grid 214 is negative biased with respect to voltage at the thermionic cathode 206.

Figure 7:
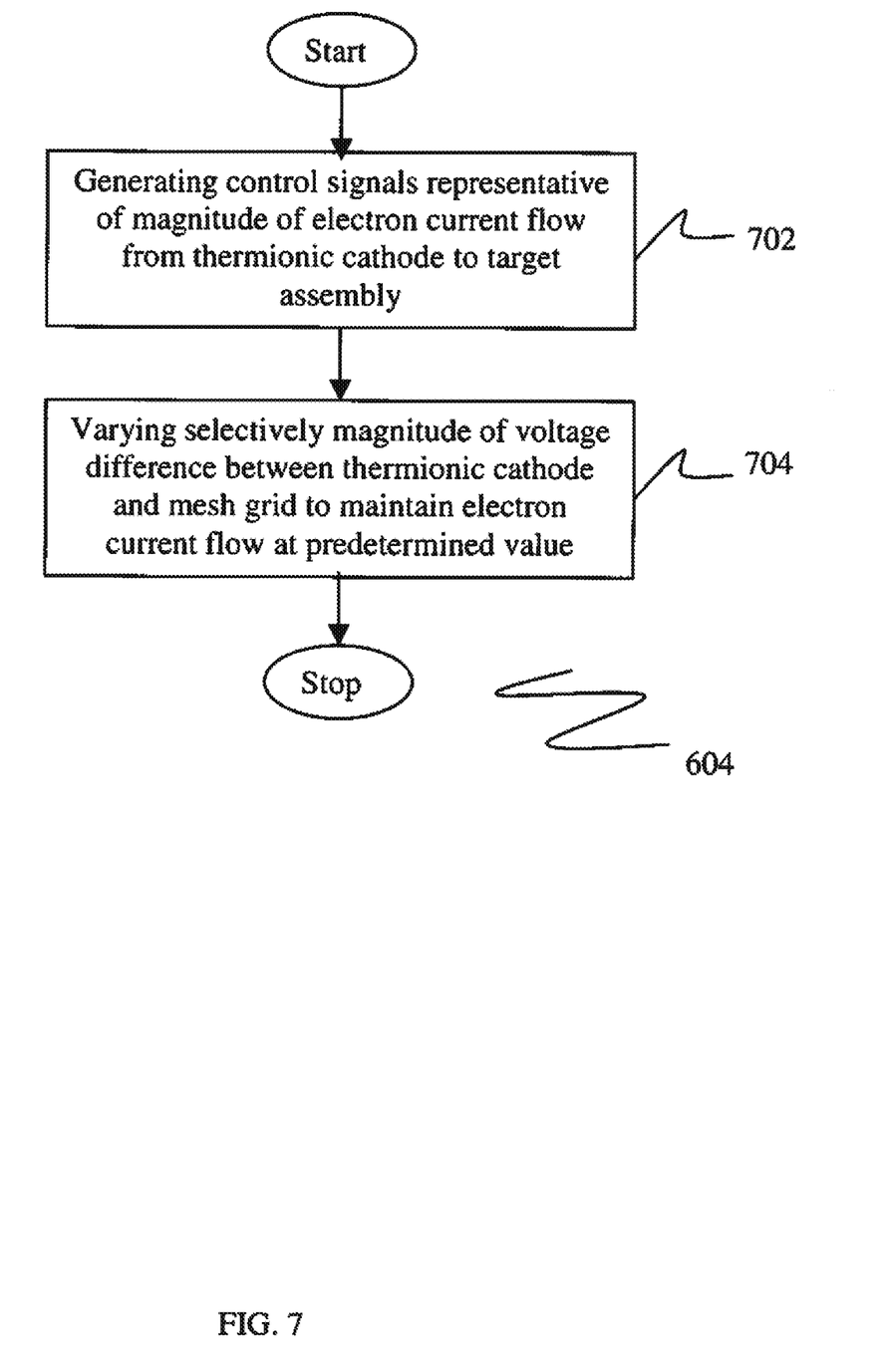
FIG. 7 shows a flow chart depicting method of modulating grid-cathode voltage described in FIG. 6.

The step 604 is further explained in conjunction with FIG. 7. As shown in FIG. 7, the method of modulating the grid-cathode voltage (step 604) comprises generating control signals representative of the magnitude of the electron current flow from the thermionic cathode 206 to the target assembly 210, at step 702 and varying selectively the magnitude of the voltage difference between the thermionic cathode 206 and the mesh grid 214 to maintain the electron current flow at a predetermined value, at step 704.

In one embodiment, the method 600 further comprises, configuring one or more pairs of focus electrodes 220 to shape the electron beam 208 such that a focal spot of the electron beam 208 has one of a predetermined size and a predetermined shape during modulation of the grid-cathode voltage.

An implementation of the system 100 and/or method 600 in an example comprises a plurality of components such as one or more of electronic components, hardware components, and/or computer software components. A number of such components can be combined or divided in an implementation of the system 100 and/or method 600. An exemplary component of an implementation of the system 100 and/or method 600 employs and/or comprises a set and/or series of computer instructions written in or implemented with any of a number of programming languages, as will be appreciated by those skilled in the art.

A technical contribution for the disclosed system 100 and/or method 600 is that it provides for a computer-implemented system and method of acquiring imaging data at more than one energy range using a multi-energy imaging source.

There are a number of potential advantages that the system 100 and method 600 described herein can bring to the CT imaging application. They are listed below.

The system and method described herein may be used in a high power medical CT X-ray tube to achieve a fast-modulated electron beam current for CT application by enabling the CT system to switch the current (mA) or voltage (kV) in high speed (view to view). This fast mA/kV modulation facilitates better image quality and enables applications like energy discriminating detectors. Energy discriminating detectors are employed in spectral CT applications where energy sensitive image can be obtained. In this application, the beam current generated at the X-ray tube is constantly adjusted such that the photo rate reaching the detector is adjusted to an optimum value.

A fast mA modulated X-ray tube helps reducing the overall X-ray dose delivered to the patient while achieving the same image quality. This dose reduction is desired when the imaging system is performing scanning around a dose-sensitive organ. In such a scenario, the X-ray dose delivered has to be carefully controlled to avoid excess radiation to the critical organs, like eyes. With fast mA modulation, it is possible to fine-tune the X-ray dose delivered when such an organ is in the scanning range. The method described herein enables complete dose managed CT that reduces the over all dose of the X-ray delivered to the patient and also the dose of the X-ray delivered to critical parts of the body.

In various embodiments of the invention, an X-ray tube for an imaging system and an imaging system using an X-ray tube are described. However, the embodiments are not limited and may be implemented in connection with different applications. The application of the invention can be extended to other areas. The invention provides a broad concept of high-speed modulation of electron beam current, which can be adapted in an industrial imaging system for thickness monitoring in process control and for use with crystal spectrometers. The design can be carried further and implemented in various forms and specifications.

This written description uses examples to describe the subject matter herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An X-ray tube comprising:
   at least one thermionic cathode having a plurality of coil windings that are configured to generate an electron beam, the plurality of coil windings having gaps between successive coil windings;
   a target assembly configured to generate X-rays when impinged with the electron beam emitted from the thermionic cathode;
   a high voltage supply unit for establishing an output voltage across the thermionic cathode and the target assembly for applying an accelerating electric field between the thermionic cathode and the target assembly; and
   a mesh grid having a plurality of grid members that correspond to the plurality of coil windings of the at least one thermionic cathode, the mesh grid disposed between the thermionic cathode and the target assembly, the mesh grid configured to operate at a voltage so as to decrease the accelerating electric field applied between the thermionic cathode and the target assembly, wherein the grid members of the mesh grid are aligned with the gaps between the successive coil windings;
   wherein the voltage of the entire mesh grid is negative biased with respect to the voltage at the thermionic cathode such that all grid members of the plurality of grid members simultaneously have a voltage applied thereto that is less than the voltage at the thermionic cathode during emission of the electron beam from the thermionic cathode to the target assembly.

2. The X-ray tube of claim 1, wherein the thermionic cathode is machined to a predetermined shape so as to control electron beam characteristics.

3. The X-ray tube of claim 1, wherein the mesh grid is a one-dimensional grid configured to focus the electron beam received from the thermionic cathode into a desired spot size.

4. The X-ray tube of claim 3, wherein the one-dimensional grid is spaced from the thermionic cathode in the range of about 0.1 mm to 1 mm.

5. The X-ray tube of claim 3, wherein the one-dimensional grid conforms to the geometry of the thermionic cathode.

6. The X-ray tube of claim 3, wherein the plurality of grid members are wires.

7. The X-ray tube of claim 6, wherein the plurality of grid members is positioned such that the grid members are parallel to one another.

8. The X-ray tube of claim 7, wherein the one-dimensional grid further comprises at least one grid member positioned perpendicular to the plurality of grid members thereby forming a plurality of openings within the mesh grid, the at least one grid member configured to provide mechanical support to the plurality of grid members.

9. The X-ray tube of claim 1, further comprising a grid-cathode voltage supply unit coupled between the mesh grid and the thermionic cathode to establish a voltage difference therebetween.

10. The X-ray tube of claim 9, wherein the amplitude of the voltage at the mesh grid is a predetermined function of time.

11. The X-ray tube of claim 10, wherein the amplitude of the voltage at the mesh grid is in the range of about +100V to −5000V relative to the voltage at the thermionic cathode.

12. The X-ray tube of claim 10, wherein the grid-cathode voltage supply unit is configured to control time variation in the amplitude of the voltage applied at the mesh grid.

13. The X-ray tube of claim 1, further comprising one or more pair of focus electrodes at least partially surrounding a perimeter of the thermionic cathode, the focus electrodes configured to shape the electron beam.

14. The X-ray tube of claim 13, wherein the mesh grid is coupled to at least one focus electrode of the one or more pair of focus electrodes.

15. The X-ray tube of claim 14, wherein the at least one focus electrode is negative biased to achieve a predetermined focal spot size and where a bias supply unit is configured to control time variation in an amplitude applied at the focus electrode.

16. The X-ray tube of claim 1 wherein the mesh grid has an aspect ratio of approximately 2 by 8.

17. The X-ray tube of claim 1 wherein the grid members of the mesh have a circular cross-sectional shape.

18. A CT system comprising:
   a rotatable gantry having an opening for receiving an object to be scanned;
   an X-ray tube coupled to the gantry and configured to project X-rays through the opening, the X-ray tube comprising:
   a housing enclosing a vacuum sealed chamber therein;
   at least one thermionic cathode located at a first end of the vacuum sealed chamber, the thermionic cathode having a plurality of coil windings that are configured to emit at least one electron beam, wherein the plurality of coil windings have gaps between successive coil windings thereof;
   a target assembly located at a second end of the vacuum sealed chamber and configured to produce X-rays when impinged with the electron beam emitted from the thermionic cathode; and
   a mesh grid disposed between the thermionic cathode and the target assembly to lower an electric field applied at a surface of the thermionic cathode, wherein the mesh grid includes a plurality of grid members, each of which corresponds with one of the gaps between the successive coil windings of the at least one thermionic cathode;

a detector assembly coupled to the gantry and positioned to receive X-rays that pass through the opening; and an image reconstructor configured to perform image reconstruction based on the received X-rays;

wherein the mesh grid is configured to concurrently operate all grid members of the mesh grid at a voltage negative biased with respect to the thermionic cathode when the electron beam is emitted from the thermionic cathode.

19. The CT system of claim 18, wherein the X-ray tube further comprises a grid-cathode voltage supply unit coupled between the mesh grid and the thermionic cathode to establish a voltage difference therebetween.

20. The CT system of claim 19, wherein the X-ray tube further comprises an input control unit coupled to the grid-cathode voltage supply unit to vary selectively a magnitude of the voltage difference between the thermionic cathode and the mesh grid so as to maintain an electron current flow from the thermionic cathode to the target assembly at a predetermined value.

21. The CT system of claim 19, wherein the grid-cathode voltage supply unit is configured to maintain voltage at the mesh grid in the range of about +100V to −5000V relative to the thermionic cathode.

22. The CT system of claim 19 wherein the voltage supply unit is configured to apply the negative biased voltage to the mesh grid as a train of pulses.

23. The CT system of claim 19 wherein the plurality of members of the mesh grid have a circular cross-sectional shape.

24. A method of X-ray imaging comprising:

arranging a thermionic cathode and a mesh grid to support a grid-cathode voltage therebetween to extract a plurality of electrons from the thermionic cathode to form an electron beam, wherein the grid-cathode voltage is defined as a voltage difference between a voltage at the mesh grid and a voltage at the thermionic cathode, wherein the thermionic cathode includes a plurality of coil windings having gaps therebetween, and wherein the mesh grid includes a plurality of grid members, each of which corresponds to a gap of the mesh grid;

generating a control signal representative of a magnitude of an electron current flow of the electron beam from the thermionic cathode to a target assembly;

modulating the grid-cathode voltage based on the control signal so as to control an amperage of the electron beam;

establishing an output voltage across the thermionic cathode and the target assembly to accelerate the electron beam toward the target assembly to generate X-rays therefrom, the target assembly positioned such that the X-rays emit toward an object;

receiving a set of imaging data indicative of an amount of attenuation of the X-rays after having passed through the object; and reconstructing an image of the object based on the imaging data received;

wherein the voltage at the mesh grid is negative biased with respect to the voltage at the thermionic cathode, and wherein each grid element of the mesh grid is maintained, at the same time, at a voltage that is less than the voltage at the thermionic cathode during acceleration of the electron beam toward the target assembly.

25. The method of claim 24, wherein the method of modulating the grid-cathode voltage further comprises:

varying selectively a magnitude of the grid-cathode voltage to maintain the electron current flow at a predetermined value.

26. The method of claim 25, further comprising configuring one or more pairs of focus and/or deflection electrodes to shape and/or deflect the electron beam such that a focal spot of the electron beam has one of a predetermined size and a predetermined position during modulation of the grid-cathode voltage.

27. The method of claim 24 wherein the mesh grid has an aspect ratio of approximately 2 by 8.

28. The method of claim 24 wherein the plurality of members of the mesh grid each have a circular cross-sectional shape.

* * * * *